(12) United States Patent
Sun et al.

(10) Patent No.: US 10,478,168 B2
(45) Date of Patent: *Nov. 19, 2019

(54) DEVICE AND METHOD FOR TREATMENT OF INCISION OR HERNIA

(75) Inventors: Wenquan Sun, Warrington, PA (US); Gary Monteiro, Grosse Pointe, MI (US)

(73) Assignee: LifeCell Corporation, Madison, NJ (US)

( * ) Notice: Subject to any disclaimer, the term of this patent is extended or adjusted under 35 U.S.C. 154(b) by 226 days.

This patent is subject to a terminal disclaimer.

(21) Appl. No.: 13/294,222

(22) Filed: Nov. 11, 2011

(65) Prior Publication Data

US 2012/0059411 A1 Mar. 8, 2012

(51) Int. Cl.
| | |
|---|---|
| *A61B 17/03* | (2006.01) |
| *A61B 17/00* | (2006.01) |
| *A61F 2/00* | (2006.01) |
| *A61L 31/00* | (2006.01) |
| *A61B 17/04* | (2006.01) |

(52) U.S. Cl.
CPC ........ *A61B 17/0057* (2013.01); *A61F 2/0063* (2013.01); *A61L 31/005* (2013.01); *A61B 17/0469* (2013.01); *A61B 2017/00606* (2013.01)

(58) Field of Classification Search
CPC ............... A61F 2/0063; A61B 17/0057; A61B 2017/00575; A61B 2017/00606; A61B 2017/00628
USPC ........................................................ 606/215
See application file for complete search history.

(56) References Cited

U.S. PATENT DOCUMENTS

| | | | |
|---|---|---|---|
| 4,813,958 A | 3/1989 | Dixon | |
| 5,254,133 A | 10/1993 | Seid | |
| 5,397,353 A | 3/1995 | Oliver et al. | |
| 5,733,337 A * | 3/1998 | Carr et al. | 435/325 |
| 6,113,623 A * | 9/2000 | Sgro | 606/215 |
| 6,171,318 B1 | 1/2001 | Kugel et al. | |
| 6,176,863 B1 | 1/2001 | Kugel et al. | |
| 6,241,768 B1 | 6/2001 | Agarwal et al. | |
| 6,383,201 B1 * | 5/2002 | Dong | 606/151 |
| 8,106,251 B2 | 1/2012 | Ayares et al. | |
| 8,324,449 B2 * | 12/2012 | McQuillan et al. | 800/17 |
| 8,357,172 B2 * | 1/2013 | Harper | 606/151 |

(Continued)

FOREIGN PATENT DOCUMENTS

| | | |
|---|---|---|
| EP | 1 421 916 A1 | 5/2004 |
| WO | WO 00/16822 | 3/2000 |
| WO | WO 2009/003726 A1 | 1/2009 |

OTHER PUBLICATIONS

Muthiah et al., Mechanical properties of skins, hides, and constituent fibres, 1967, Biorheology, Sep;4(4):185-91.*

(Continued)

*Primary Examiner* — Todd J Scherbel
(74) *Attorney, Agent, or Firm* — McCarter & English, LLP; Matthew R. Van Eman; George Blazeski (57) ABSTRACT

Devices and methods for treating an abdominal incision or hernia are described. An implant for the restoration or prophylactic treatment of an abdominal wall comprises an elongate element and at least one sheet connected to the elongate element along a longitudinal axis of the elongate element. The elongate element is positioned along the line of incision, and the at least one sheet is secured to the abdominal muscles surrounding the incision.

25 Claims, 6 Drawing Sheets

(56) References Cited

U.S. PATENT DOCUMENTS

| | | | |
|---|---|---|---|
| 10,238,480 | B2 | 3/2019 | Harper |
| 2003/0023316 | A1 | 1/2003 | Brown et al. |
| 2003/0225355 | A1 | 12/2003 | Butler |
| 2004/0098042 | A1 | 5/2004 | Devellian et al. |
| 2004/0209538 | A1 | 10/2004 | Klinge et al. |
| 2004/0260315 | A1* | 12/2004 | Dell et al. .................. 606/151 |
| 2005/0043818 | A1 | 2/2005 | Bellon Caneiro et al. |
| 2005/0240075 | A1 | 10/2005 | Li |
| 2007/0118176 | A1 | 5/2007 | Opolski et al. |
| 2009/0234461 | A1 | 9/2009 | Rehnke |
| 2010/0082114 | A1 | 4/2010 | Gingras et al. |
| 2010/0124563 | A1 | 5/2010 | Coleman et al. |
| 2010/0185219 | A1 | 7/2010 | Gertzman et al. |
| 2011/0004306 | A1* | 1/2011 | Harper ..................... 623/14.13 |
| 2011/0015760 | A1* | 1/2011 | Kullas ...................... 623/23.72 |
| 2012/0059411 | A1 | 3/2012 | Sun et al. |
| 2012/0221118 | A1* | 8/2012 | Bartee et al. ............. 623/23.72 |
| 2013/0103061 | A1* | 4/2013 | Harper ........................ 606/151 |

OTHER PUBLICATIONS

Merriam-Webster Dictionary, Tensile Strength, http://www.merriam-webster.com/dictionary/tensile%20strength as accessed on Jul. 30, 2015.*

The Free Dictionary by Farlex, definition of "spine", http://medical-dictionary.thefreedictionary.com/spine as accessed on Jun. 15, 2016.*

The Free Dictionary by Farlex, definition of "caudal", http://medical-dictionary.thefreedictionary.com/caudal as accessed on Jun. 15, 2016.*

Gobin et al., Repair and Regneration of the Abdominal WAll Musculofascial Defect Using Silk Fibroin-Chitosan Blend, 2006, Tissue Engineering, vol. 12, No. 12, pp. 3383-3394.*

Burns et al., Non-Cross-Linked Porcine Acellular Dermal Matrices for Abdominal Wall Reconstruction, 2009, Plastic and Reconstructive Surgery, vol. 125, No. 1, pp. 167-176.*

Bulter et al., Comparison of Cross-Linked and Non-Cross-Linked Porcine Acellular Dermal Matrices for Ventral Hernia Repair, Journal of the American College of Surgeons, vol. 211, Issue, 3, pp. 368-376 (Sep. 3, 2010).*

Ankersen et al., Puncture resistance and tensile strength of skin simulants, 1999, Proc Instn Mechn Engrs, vol. 213, Part H, pp. 493-501.*

International Search Report and Written Opinion issued by European Patent Office for International Application No. PCT/US2010/040717, dated Sep. 28, 2010.

Dai, Y. et al., "Targeted disruption of the α1,3-galactosyltransferase gene in cloned pigs," Nat. Biotechnology 20, 251-255 (2002).

Phelps, C. J. et al., "Production of α1,3-Galactosyltransferase-Deficient Pigs," Science 299, 411-414 (2003).

Voyles C. R. et al., "Emergency Abdominal Wall Reconstruction with Polypropylene Mesh," Ann. Surg. 194(2), 219-223 (1981).

De Vries Reilingh T. S. et al., "Repair of Giant Midline Abdominal Wall Hernia: 'Components Separation Technique' versus Prosthetic Repair," World J. Surg 31, 756-763 (2007).

Final Office Action dated Oct. 29, 2013 in U.S. Appl. No. 13/714,606.

Burns, Nadja K., et al., "Non-Cross-Linked Porcine Acellular Dermal Matrices for Abdominal Wall Reconstruction", *Plast Reconstr Surg.* 2009: PMID:19910855.

Connor, J. et al., "Retention of Structural and Biochemical Integrity in a Biological Mesh Supports Tissue Remodeling in a Primate Abdominal Wall Model", *Regen Med.* 2009:4(2):185-195.

Xu, Hui, et al., "A Porcine-Derived Acellular Dermal Scaffold That Supports Soft Tissue Regeneration: Removal of Terminal Galactose-α-(1,3)-Galactose and Retention of Matrix Structure", *Tissue Engineering*: Part A, vol. 15, No. 7, 2009, pp. 1807-1819.

Sandor, Maryellen, et al., "Host Response to Implanted Porcine-Derrived Biologic Materials in a Primate Model of Abdominal Wall Repair", *Tissue Engineering: Part A*, vol. 14, No. 12, 2008, pp. 2021-2031.

Butler, Charles E., "The Role of Bioprosthetics in Abdominal Wall Reconstruction", *Clin Plastic Surg*, 33, 2006, pp. 199-211.

Capito, Anthony E., et al., "Evaluation of Host Tissue Integration, Revascularization, and Cellular Infiltration Within Various Dermal Substrates", *Annals of Plastic Surgery*, vol. 68, No. 5, May 2012, pp. 495-500.

Menon, N. G., "Revascularization of Human Acellular Dermis in Full-Thickness Abdominal Wall Reconstruction in the Rabbit Model", *Ann Plast Surg.* 2003; 50(5):pp. 523-527. Erratum in Ann Plast Surg. 2003; August 51(2): p. 228.

Buinewicz, B., et al., "Accellular Cadaveric Dermis (AlloDerm): A New Alternative for Abdominal Hernia Repair", *Annals of Plastic Surgery*, vol. 52, No. 2, Feb. 2004, pp. 188-194.

Kolker, A. R., et al., "Multilayer Reconstruction of Abdominal Wall Defects With Acellular Dermal Allograft (AlloDerm) and Component Separation", *Annals of Plastic Surgery*, vol. 55, No. 1, Jul. 2005, pp. 36-42.

Silverman, R. P., et al., Ventral hernia repair using allogenic acellular dermal matrix in a swine model, *Hernia*, (2004) 8: pp. 336-342.

U.S. Appl. No. 13/714,606, filed Dec. 14, 2014, US 2013/0103061.

Egorov et al., Mechanical properties of the human gastrointestinal tract. J Biomech. Oct. 2002;35(10):1417-25.

Harty et al., Regeneration or scarring: an immunologic perspective. Dev Dyn. Feb. 2003;226(2):268-79.

MakeItFrom.com, Polyglycolic Acid (PGA, Polyglycolic). Retrieved online at: http://www.makeitfrom.com/material-properties/Polyglycolic-Acid-PGA-Polyglycolide/ 2 pages, 2009-2015.

\* cited by examiner

DEVICE AND METHOD FOR TREATMENT OF INCISION OR HERNIA

This disclosure relates generally to devices and methods for treating abdominal incisions or defects, and more particularly, to prosthetic devices for treating midline incisions or hernias.

Most surgical incisions can be closed using only sutures. However, closing an abdominal incision in patients suffering from gross abdominal wall loss, particularly loss of viable fascial tissue, due, for example, to prior surgeries or necrotizing infection, can be challenging. In addition, some patients may be prone to dehiscence and/or herniation after surgery due to structural defects or disease.

Currently, repair of abdominal wall incisions not amenable to primary suture closure is sometimes performed using a synthetic mesh (such as, polypropylene, prolene, polytetrafluroethylene meshes, etc.) to reinforce the fascia and restore abdominal wall continuity. However, for many patients, incision closure and treatment of abdominal wall defects remains difficult, particularly due to the complications resulting from synthetic mesh use, such as enteric fistulae formation and infection, which weaken the integrity of the incision closure.

The present disclosure provides methods and devices for improved closure of surgical incisions and/or repair of abdominal wall defects.

In one aspect of the present disclosure, a device for treating abdominal incision or hernia is provided. The device comprises an elongate element having a first longitudinal axis and at least one sheet connected to the elongate element along the first longitudinal axis, wherein the at least one sheet comprises an acellular dermal tissue matrix and the elongate element has a biomechanical strength that is at least equal to that of the at least one sheet.

In another aspect of the present disclosure, a method for treating a midline incision is provided. The method includes providing an implant comprising an elongate element having a first longitudinal axis and at least one sheet connected to the elongate element along the first longitudinal axis, wherein the at least one sheet comprises an acellular dermal tissue matrix. The elongate element is positioned along the midline incision, and the at least one sheet is positioned on the anterior and/or posterior sides of rectus abdominis muscle surrounding the midline incision.

It is to be understood that both the foregoing general description and the following detailed description are exemplary and explanatory only and are not restrictive of the invention, as claimed.

The accompanying drawings, which are incorporated in and constitute a part of this specification, illustrate methods and embodiments of the invention and together with the description, serve to explain the principles of the various aspects of the invention.

DESCRIPTION OF EXEMPLARY EMBODIMENTS

Reference will now be made in detail to embodiments consistent with the present disclosure, examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit, unless specifically stated otherwise. Also the use of the term "portion" may include part of a moiety or the entire moiety. Additionally, in this application, the terms "rectus sheath" and "rectus fascia" may be used interchangeably, unless specifically stated otherwise.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The present disclosure provides methods and devices for effective incision closure following a surgical procedure and/or abdominal wall treatment for structural abdominal wall defects. In one aspect, the devices and methods disclosed herein are used for closing abdominal incisions when primary suture closure is not feasible due to loss of abdominal muscle and/or fascia. In some embodiments, the devices and methods disclosed herein are used for midline incision closure following a surgical procedure. In another aspect, the devices and methods are used as a treatment for ventral or incisional hernia, e.g., for treatment of midline incisional hernia. In various embodiments, the methods and devices of the present disclosure can be used for prophylactic treatment, e.g., to prevent incisional hernia. In some embodiments, the methods and devices of the present disclosure can be used to treat preexisting abdominal wall defects or to assist in closure of incisions or hernias where insufficient abdominal tissue is present.

In one exemplary embodiment of the present disclosure, incision closure is performed using an implant comprising an elongate element and at least one sheet connected to the elongate element along a longitudinal axis of the elongate element. When performing an incision closure, the elongate element is positioned along the incision line, and the at least one sheet is positioned on the anterior and/or posterior side of the abdominal muscles surrounding the incision. In one embodiment, the biomechanical properties (e.g., the tensile strength, compressive strength, torsional strength, toughness of the material, etc.) of the elongate element are equal to that of the at least one sheet. In another embodiment, certain biomechanical properties (e.g., tensile strength, stiffness, tear strength) of the elongate element are greater than that of the at least one sheet. The relative mechanical properties of the elongate element and the sheet may be determined based on the specific application of the implant. For example, in one embodiment, a strength of the elongate element is twice that of the at least one sheet. In another embodiment, a strength of the elongate element is at least three times that of the at least one sheet.

In one exemplary embodiment, the sheet comprises a porous biological material. In some embodiments, the sheet comprises a collagenous material. In certain embodiments, the sheet comprises an acellular tissue matrix, which may support revascularization and repopulation of the implanted matrix with the patient's own cells to further strengthen the treatment site and lower the risk of matrix dislodgement. In some embodiments, the acellular tissue matrix includes a dermal matrix. In one such embodiment, the sheet is derived from human skin (e.g. ALLODERM®, LifeCell Corp, Branchburg, N.J.) that has been processed to remove both the epidermis and the cells that can lead to tissue rejection and graft failure, without damaging the dermal matrix. In another embodiment, the sheet is derived from porcine dermis (e.g. STRATTICET™, LifeCell Corp, Branchburg, N.J.), which is processed to remove cells and tissue antigens while maintaining the ability to support cellular growth and tissue regeneration and/or remodeling. In exemplary embodiments, the acellular dermis matrix is derived from skin harvested from the spinal region of human, porcine, bovine, or other animals. Dermal matrix sheets collected from the spinal region of an animal have higher tensile strength, show less variation in biomechanical properties, and are less stretchy as compared to dermis sheets harvested from other parts of the animal. Table 1 demonstrates the difference in certain biomechanical properties of acellular human dermis, acellular porcine dermis (from non-spinal region), and acellular porcine dermis harvested from the spinal region. Each of the test specimens were cut into 6.0 cm×1.0 cm strips with a thickness between 1.1 mm to 1.5 mm. A uniaxial tensile test was done using an instron machine with a gage length of 40 mm, and a strain rate of 1.5 mm/mm/s. The stretchability of the tissue specimen (percentage of deformation in length) was measured using a constant force of 5 N/cm. As shown in Table 1, dermal tissue matrices from the porcine spinal region have a higher tensile strength and Young's modulus, are less stretchable, and show a lower variation in stretchability (i.e., the amount of tissue deformation is more consistent) as compared to dermal tissue from non-spinal regions.

TABLE 1

Comparison of Biomechanical Properties of Dermal Tissue Collected from Different Sources

| | Tensile Strength (MPa) | Young's Modulus (Mpa) | Stretch (%) |
| --- | --- | --- | --- |
| Human dermis from non-spinal region (n = 125) | 14.2 ± 6.5 | 51.0 ± 27.2 | 29.0 ± 16.0 |
| Porcine dermis from non-spinal region (n = 912) | 9.3 ± 3.8 | 34.8 ± 18.4 | 17.0 ± 6.0 |
| Porcine dermis from spinal region (n = 39) | 18.1 ± 4.8 | 72.1 ± 22.6 | 7.0 ± 2.8 |

In another exemplary embodiment of the present disclosure, the sheet of the implant comprises a porous synthetic mesh (e.g., polypropylene, prolene, or polytetrafluroetheylene mesh). In one such embodiment, the synthetic mesh facilitates tissue incorporation into the implant.

In one exemplary embodiment consistent with the present disclosure, the elongate element is a cylindrical body comprising an immunologically inert and biocompatible material. The material may be a synthetic polymer (such as, polypropylene, polytetrafluroetheylene, etc.) or a non-synthetic material. In one embodiment of the present disclosure, the elongate element comprises a biological mesh that is rolled concentrically into a cylindrical structure. In one such embodiment, the biological mesh comprises an acellular tissue matrix (such as, ALLODERM® or STRATTICE™). In another embodiment, the biological mesh comprises an acellular tissue matrix derived from skin harvested from the spinal region of human, porcine, bovine, or other animals. In one exemplary embodiment, the biological mesh is rolled into a 6 cm cylindrical core of approximately 1 cm in diameter.

In various embodiments consistent with the present disclosure, the elongate element and sheets can be produced from tissue that is allogeneic or xenogenic to a human recipient. Allogeneic sources may be obtained from living donors or cadavers. Xenogeneic sources can include a variety of different non-human mammals. For example, as noted above, one suitable biologic material for production of the sheets and elongate element is STRATTICE™, which is a porcine-derived tissue matrix. However, other xenograft sources can be used.

Allogeneic or xenogenic tissues can be processed to remove antigens known to elicit an immune response in the recipient. For example, various decellularization processes or enzyme treatments are known that allow removal of cellular and/or extracellular antigens that may be immunogenic. Further, in various embodiments, the tissues can be derived from animals that are genetically modified or altered to have diminished expression of antigens known to be immunogenic in humans. For example, in one such embodiment, the tissues are harvested from an α1,3-galactosyltransferase (α1,3GT) deficient pig or other animal to prevent hyperacute rejection of the implant by the recipient. Different methods of producing α1,3GT deficient pigs have been previously described in Dai, Y. et al., "Targeted disruption of the α1,3-galactosyltransferase gene in cloned pigs," *Nat. Biotechnology* 20, 251-255 (2002), and Phelps, C. J. et al., "Production of α1,3-galactosyltransferase-deficient pigs," *Science* 299, 411-413 (2003), which are incorporated herein by reference.

In some embodiments of the present disclosure, the elongate element can include a strip or piece of connective tissue from an allogeneic or xenogeneic source. For example, suitable connective tissues can include ligament, tendon, and/or fascia. In exemplary embodiments, the piece of connective tissue is decellularized prior to its application as an elongate element in the prosthetic implant. In certain embodiments, the piece of connective tissue forming the elongate element has biomechanical properties (e.g., the tensile strength, stretchability, etc.) that are equal or substantially close to that of the at least one sheet. This helps in stabilizing the elongate element in the surgical incision or abdominal wall defect, and facilitates mechanical load sharing between the elongate element and the at least one sheet during the wound healing process. In an exemplary embodiment, the at least one sheet comprises an acellular dermal tissue matrix from the spinal region of an animal and the elongate element comprises an acellular ligament or tendon, since the biomechanical properties of dermis sheets from the spinal region are closely comparable to that of acellular ligaments or tendons.

In one exemplary aspect of the present disclosure, the prosthetic implant is used for treatment of a midline abdominal incision, which is a vertical incision made along the linea alba between the two rectus abdominis muscles of the abdominal wall. In certain patients, the linea alba may be absent or shifted from the abdominal midline due to abdominal wall defects. In such cases, the midline incision may be performed along the anatomical midline of the abdominal wall, instead of the linea alba (if present). When closing the midline incision, the elongate element is positioned along the incision, and the at least one sheet is positioned over and/or under the rectus abdominis muscles surrounding the incision. The linea alba located in the abdominal midline is a three-dimensional composition of connective tissue fibers from abdominal wall muscles, which plays a significant role in stabilizing the abdominal wall. Use of a connective tissue material for the elongate element, therefore, facilitates reliable closure of the midline incision and provides good aesthetic results. The elongate element may, however, comprise any biological or synthetic material that is immunologically compatible, is structurally and functionally similar to the linea alba, and facilitates duplication of the abdominal wall physiology.

Figure 1A:
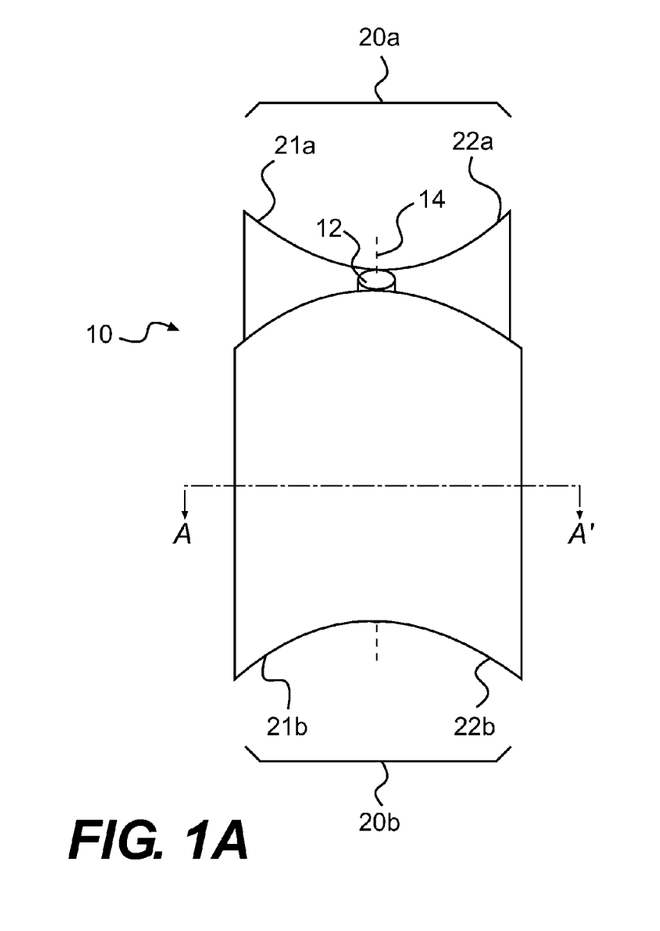
FIG. 1A shows an exemplary embodiment of an implant for treatment of an incision or hernia.
Figure 1B:
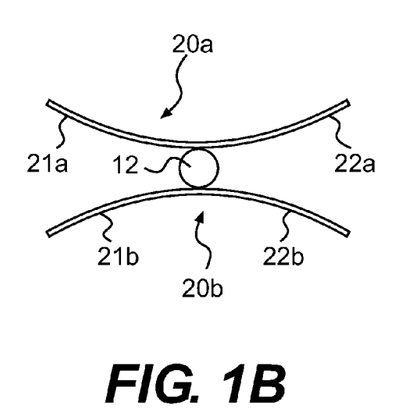
FIG. 1B is a cross-sectional view of the embodiment depicted in FIG. 1A taken along line AA'.
Figure 1C:
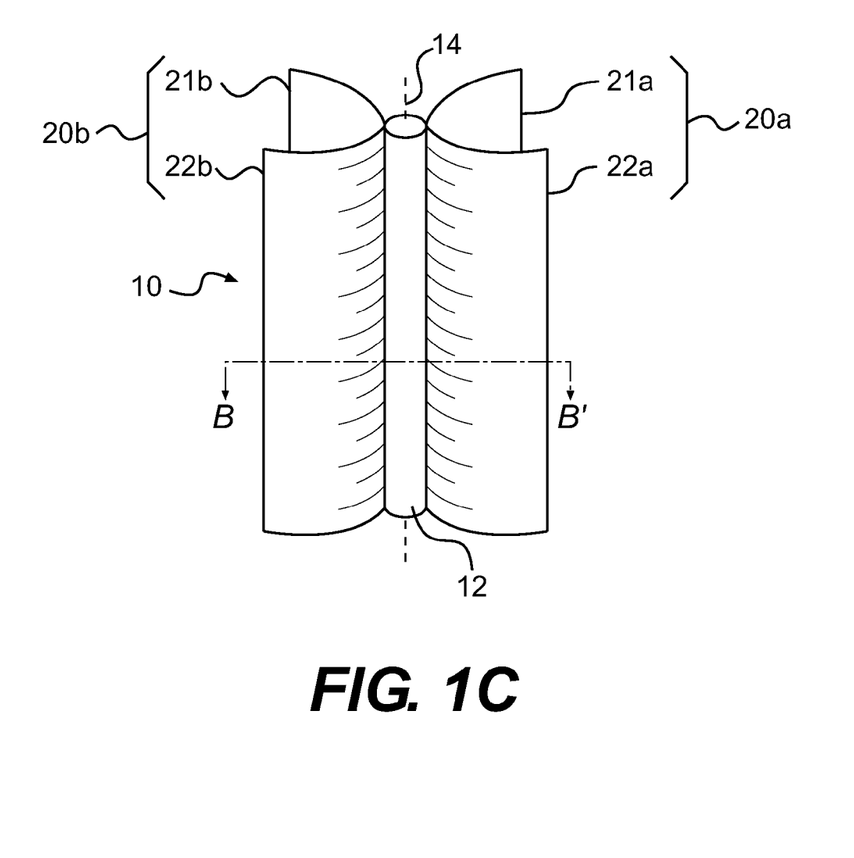
FIG. 1C depicts an alternate configuration of the implant depicted in FIG. 1A.
Figure 1D:
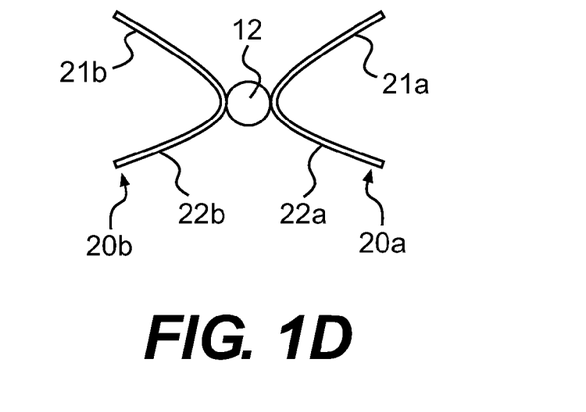
FIG. 1D is a cross-sectional view of the configuration depicted in FIG. 1C taken along line BB'.

FIG. 1A shows an exemplary embodiment of a prosthetic implant 10 in accordance with the present disclosure. FIG. 1B illustrates a cross-sectional view of the embodiment depicted in FIG. 1A taken along line AA'. FIG. 1C depicts an alternate configuration of implant 10, and FIG. 1D is a cross-sectional view of the configuration depicted in FIG. 1C taken along line BB'. Implant 10 comprises an elongate element 12 and at least two sheets 20a and 20b connected to the outer surface of elongate element 12 on opposite sides of a longitudinal axis 14 of the central element. The sheets can be connected to elongate element 12 using absorbable biological sutures (e.g. catgut, polyglactin, etc.), non-absorbable sutures (e.g. nylon, polypropylene, etc.), surgical staples, clips, or tissue adhesives. In one embodiment, as illustrated in FIG. 1A-1D, sheets 20a and 20b are connected to elongate element 12 along the midline of the sheets. In such an embodiment, attachment of sheets 20a and 20b to elongate element 12 divides the sheets into two halves.

As depicted in FIGS. 1A-1D, sheet 20a forms two flaps 21a and 22a of equal dimensions upon attachment to element 12. Similarly, sheet 20b forms two symmetrical flaps 21b and 22b. Sheets 20a and 20b may, however, be connected to elongate element 12 along any longitudinal axial line of the sheets. In some embodiments consistent with the present disclosure, the flaps formed by connection of the sheets to the elongate element are asymmetrical.

In one embodiment, sheets 20a and 20b extend along a plane substantially parallel to longitudinal axis 14, as illustrated in FIGS. 1A and 1B. In such an embodiment, sheets 20a and 20b form two pockets between flaps 21a and 21b and 22a and 22b, respectively, when attached to elongate element 12. In an alternate embodiment, sheets 20a and 20b are folded away from elongate element 12, as illustrated in FIG. 1C and FIG. 1D, such that sheets 20a and 20b form two pockets between flaps 21a and 22a and 21b and 22b, respectively.

Although sheets 20a and 20b are generally shown in a rectangular form in the figures, the depiction is only for illustrative purposes, and any suitable size, shape and form can be used depending upon the specifications of the surgical procedure and the extent of repair necessary. In one embodiment, as illustrated in FIGS. 1A and 1C, the lengths of both sheets 20a and 20b are equal to the length of elongate element 12. The lengths of elongate element 12 and sheets 20a and 20b are selected to span the length of the incision. However, in some embodiments, the length of implant 10 may be shorter than the length of the incision, depending on the extent of the restorative procedure and the amount of reinforcement required in the abdominal wall. The geometry of implant 10 may be tailored to the intended application prior to the surgery or during the surgical procedure. Further, in some embodiments consistent with the present disclosure, implant 10 comprises multiple sheets that are superimposed, or layered, to provide additional reinforcement to the abdominal wall. The multiple sheets may be chemically or physically bonded to each other to facilitate positioning of implant 10 in the abdominal wall.

Figure 2A:
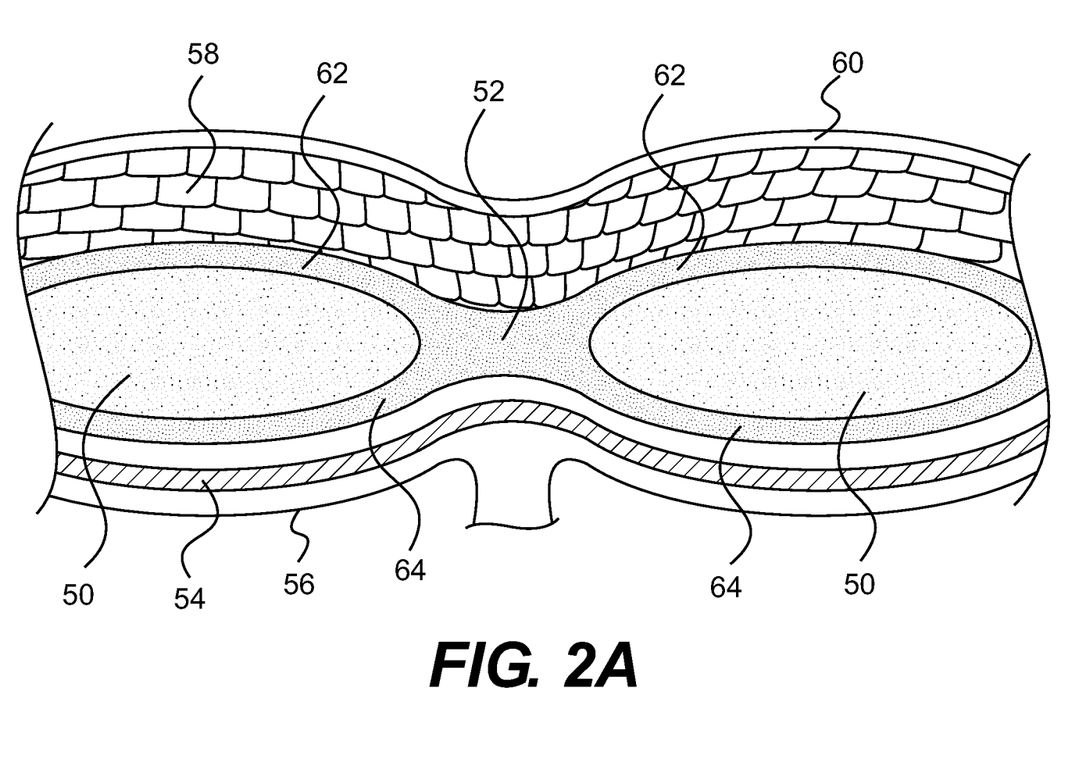
FIG. 2A is a cross-sectional view of the abdominal wall.
Figure 2B:
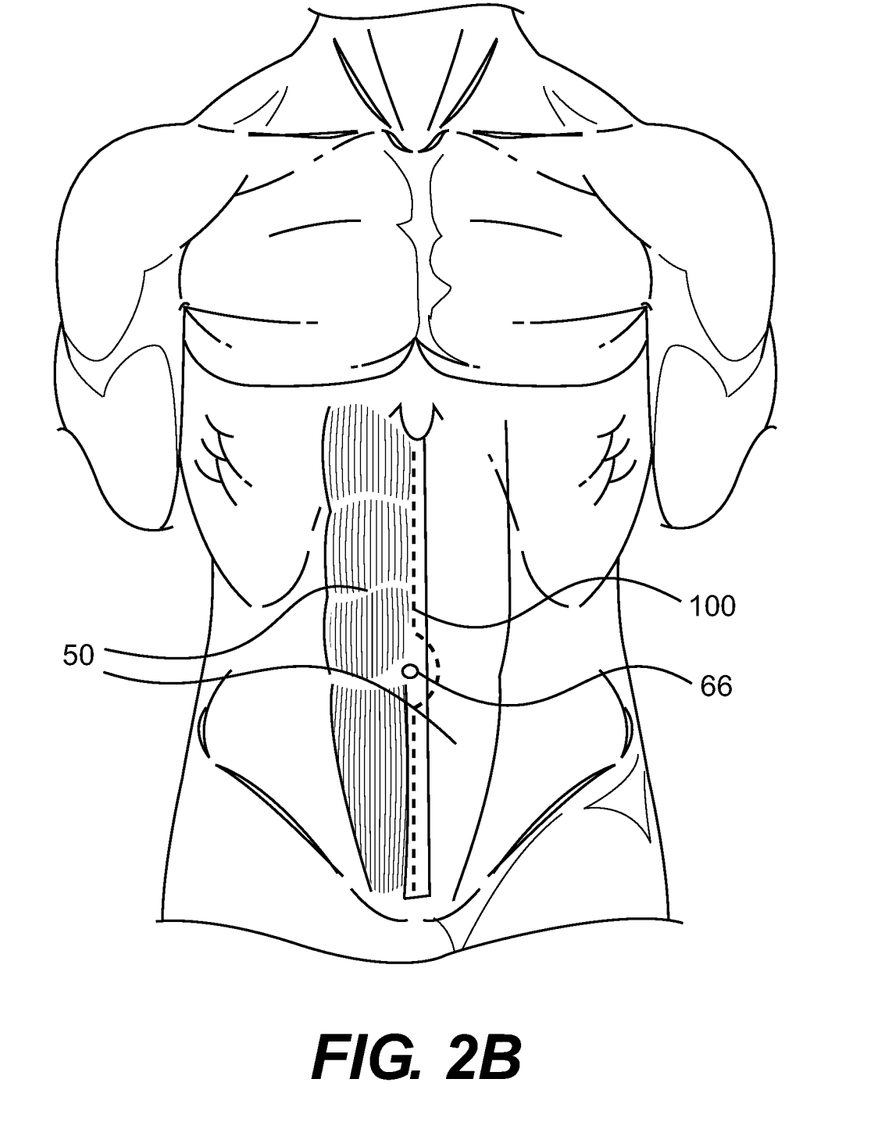
FIG. 2B illustrates an outline of a midline abdominal incision.

The method of performing an incision closure using prosthetic implant 10 will now be described with reference to FIGS. 2A and 2B, which illustrate the anatomy of the abdominal wall and an abdominal midline incision outline, respectively. FIG. 2A shows a cross-sectional view of the abdominal wall comprising the rectus abdominis muscles 50, linea alba 52, transversalis fascia 54, peritoneum 56, subcutaneous fat 58, skin 60, anterior layer of fascia 62 and posterior layer of fascia 64. FIG. 2B shows a midline incision 100 made through linea alba 52 between rectus abdominis muscles 50 and around umbilicus 66. Further, although this method is described for midline closure, the method of incision closure disclosed can be applied for the treatment of any incision type and/or to treat other structural abdominal wall defects.

Figure 3A:
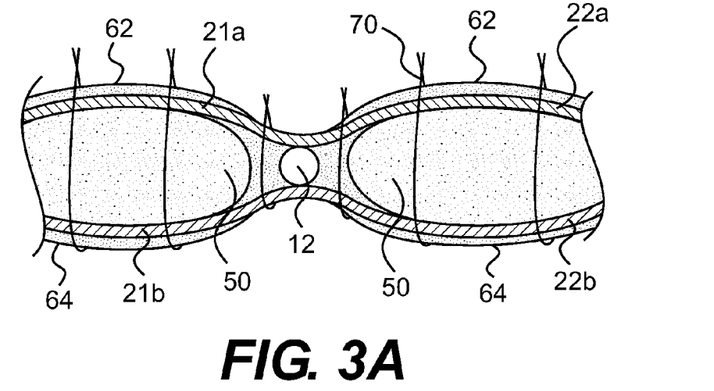
FIG. 3A shows a method of positioning an implant in the abdominal wall for a midline incision closure, in accordance with an exemplary embodiment of the present disclosure.

During closure of midline incision 100, elongate element 12 of implant 10 is positioned along the line of incision, and sheets 20a and 20b are positioned on the anterior and/or posterior sides of rectus abdominis muscles 50. Prior to the positioning of elongate element 12, potential spaces for the placement of the sheets 20a and 20b may be created by dissection around the incision using a blunt instrument or the surgeon's fingers. In one embodiment of the present disclosure, when the midline incision is above the arcuate line of the abdomen, spaces between the rectus abdominis muscles 50 and the anterior and posterior layers of fascia 62, 64 may be dissected for placement of the sheets 20a and 20b. Elongate element 12 is then aligned with the midline incision, and the sheets are inserted into the dissected pockets, as shown in FIG. 3A. Below the arcuate line, the posterior layer of fascia 64 is not present, and therefore, the posterior flaps 21b and 22b are positioned in spaces dissected between rectus abdominis muscles 50 and transversalis fascia 54 or positioned to cover the transversalis fascia 54 or peritoneum 56.

Figure 3B:
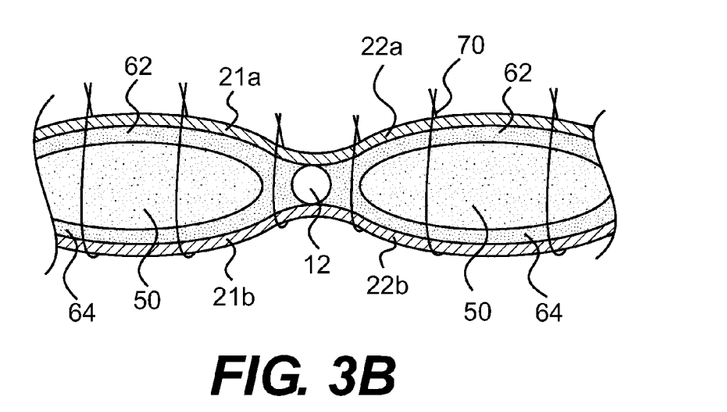
FIG. 3B illustrates an alternate method of positioning an implant in the abdominal wall for a midline incision closure, in accordance with an exemplary embodiment of the present disclosure.

In another embodiment of the present disclosure, as illustrated in FIG. 3B, sheets 20a and/or 20b overlay anterior layer of fascia 62, and on the posterior side, the sheets are positioned between posterior layer of fascia 64 and transversalis fascia 54 or overlying the transversalis fascia or peritoneum.

In some patients receiving implant 10, the anterior and/or posterior layers of fascia 62, 64 may be partially or completely lost due to multiple prior surgeries, necrotizing infections, and/or other complications. In such cases, sheets 20a and 20b are simply positioned in proximity to the rectus muscles 50. If the fascia is partially present, it may be abraded by the surgeon to expose the rectus muscles and release blood to initiate the would healing process. The sheets then spontaneously anneal with the rectus muscles. When the sheets comprise a biological matrix material, the sheets may be remodeled by the patient's own cells, thereby, facilitating rapid integration of the sheets into the repair site.

In another embodiment of the present disclosure, elongate element 12 is aligned with the midline incision in accordance with the configuration shown in FIGS. 1C and 1D, such that the rectus muscles 50 are supported between flaps 21a and 22a of sheet 20a on one side of the incision, and flaps 21b and 22b of sheet 20b on the other side.

Following the placement of sheets 20a and 20b into the treatment site, the sheets are secured to the rectus muscles. The sheets 20a and 20b can be secured using a variety of anchoring systems, including, for example, sutures, staples, clips, and/or tissue adhesives. As used herein, securing the sheets 20a and 20b to the rectus muscles will be understood to include securing the sheets 20a and 20b directly to the rectus muscles and to include securing the sheets to a layer of the abdominal wall adjacent to the rectus muscles, including a layer of rectus fascia, transversalis fascia, or peritoneum.

In some embodiments, as shown in FIGS. 3A and 3B, the sheets are secured using sutures that pass through a portion of the sheet, the rectus abdominis muscles, and/or the posterior and/or anterior layer of fascia. The suturing needle is inserted through layers of the abdominal wall and sheets 20a and 20b, and then reversed to retrace the path through the abdominal wall layers and sheets. The free ends of sutures 70 are tied together on the anterior side of sheets 21a and 22a. In some embodiments, as shown in FIG. 3A, the sutures may be tied anterior to the anterior layer of fascia 62. Sufficient care is taken to avoid incorporation of visceral or other structures into the suture line. Sutures are placed along the line of incision to ensure complete reapproximation of the abdominal wall. The frequency of the lateral suture anchors is determined by the surgeon during the procedure.

Figure 4:
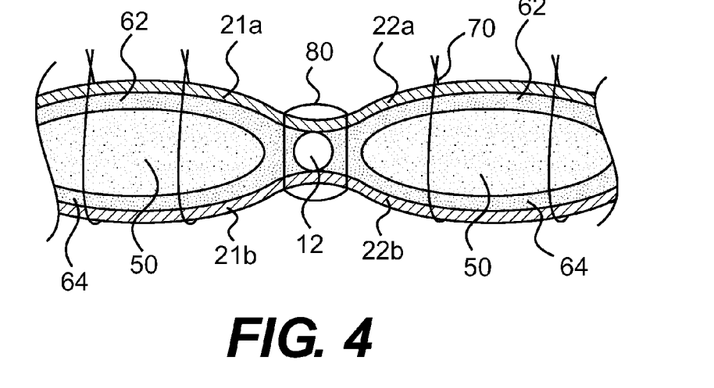
FIG. 4 illustrates a method of suturing an implant to the abdominal wall for a midline incision closure, in accordance with an exemplary embodiment of the present disclosure.

In some embodiments, the reapproximation is performed using continuous or interrupted loop sutures 80, as shown in FIG. 4. Suture loops 80 incorporate elongate element 12 in order to secure the fascia and or rectus muscles to the elongate element 12. This applies tension to the abdominal wall structures and draws them medially to close the incision. Loop sutures 80 may be used in conjunction with interrupted sutures 70, as described above, or alone.

Figure 5:
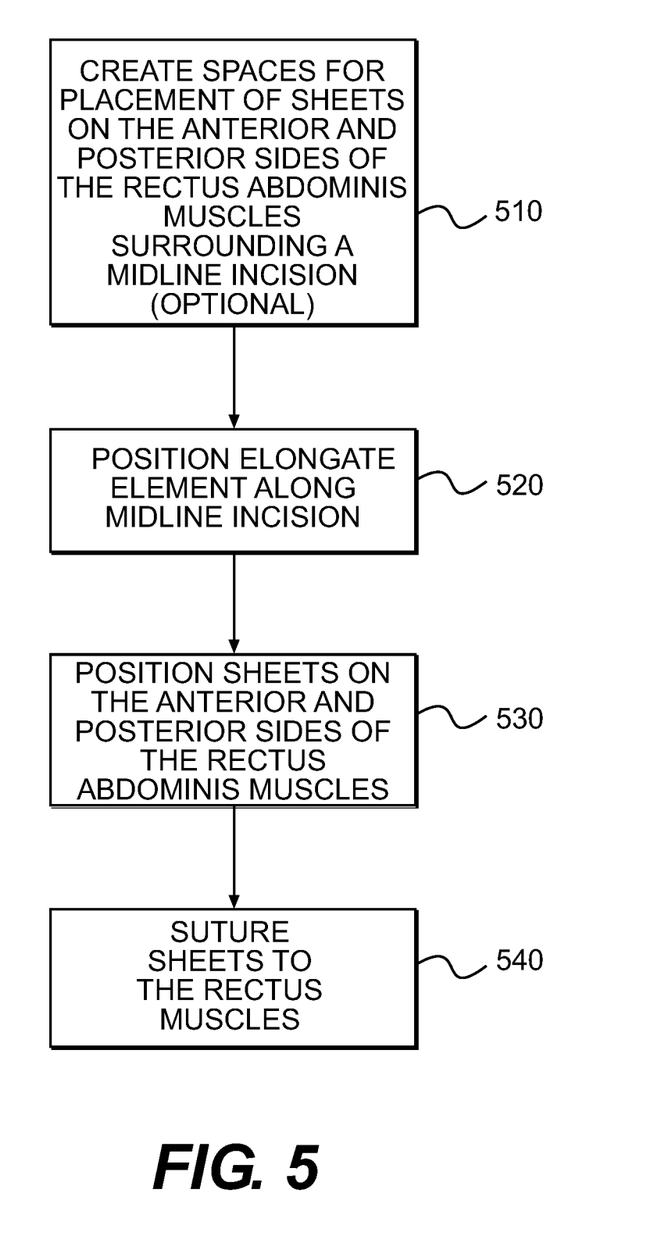
FIG. 5 is a flowchart showing the steps of treating an abdominal incision using an exemplary implant of the present disclosure.

FIG. 5 is a flowchart diagramming the steps of treating an abdominal wall following a midline incision using implant 10. As noted, the method can be used for prophylactic treatment of the incision (e.g., to prevent dehiscence) or to facilitate closure of incisions or defects that are difficult to close with sutures alone.

The first step in closing the midline incision includes optionally creating potential spaces for the placement of sheets 20a and 20b on both sides of the midline incision (step 510) if needed. In one aspect of the present disclosure, spaces between rectus muscles 50 and anterior layer of fascia 62 are dissected for placement of the sheets on the anterior side of the ventral abdominal wall, and spaces between rectus muscles 50 and posterior layer of fascia 64 or transversalis fascia 54 are created for placement of the sheets in the posterior side of the abdominal wall. In another aspect, the sheets are positioned over anterior layer of fascia 62 and below posterior layer of fascia 64. In such a procedure, the surgeon creates spaces between fascia 62 and subcutaneous fat 58 on the anterior side on the abdominal wall. On the posterior side, spaces between fascia 64 or rectus muscles 50 and transversalis fascia 54 may be dissected. Alternatively, on the posterior side, the sheets 20a and/or 20b may be placed between the transversalis fascia and the peritoneum. Step 510 may not be required if an adequate region for attachment of the sheets to rectus abdominis muscles is already present or if a patient is suffering from substantial loss of fascia 62, 64.

The second step comprises positioning elongate element 12 of implant 10 along the midline incision (step 520) to begin approximation of the wound margins. In one exemplary embodiment, the cranial end of elongate element 12 is aligned with the superior end of the midline incision, and the caudal end of the implant is aligned with the inferior end of the incision. The size of the implant could be adjusted by the surgeon either before the procedure, or during the placement of the implant.

The next step is the insertion of the sheets into the spaces created in step 510 (step 530) or on the appropriate sides of the rectus muscles if no spaces have been created.

Next, the sheets are secured in place (step 540). As described above, the sheets can be secured using, sutures, staples, clips, tissue adhesives, or other suitable means. The method of securing the device and the suturing technique are determined by the surgeon during the procedure. This is followed by closure of the skin using either non-absorbable or absorbable sutures. Alternatively, surgeons may use surgical staples for skin closure due to speed of application and ease of removal.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A device for treating an incision, hernia, or abdominal wall defect, comprising:
    an elongate element having a first longitudinal axis; and
    at least one sheet connected to the elongate element along the first longitudinal axis;
        wherein the at least one sheet comprises an acellular dermal tissue matrix derived from porcine dermis having a Young's modulus within a range of 49.5 MPa to 94.7 MPa.

2. The device of claim 1, wherein the at least one sheet is connected to the elongate element along an approximate midline of the sheet.

3. The device of claim 1, wherein the tissue is from an α1,3-galactosyltransferase (α1,3GT) deficient pig.

4. The device of claim 1, wherein the elongate element comprises an acellular dermal tissue matrix.

5. The device of claim 4, wherein the elongate element comprising the acellular dermal tissue matrix is rolled concentrically into a cylindrical structure.

6. The device of claim 1, wherein the elongate element comprises a piece of acellular connective tissue.

7. The device of claim 6, wherein the connective tissue is a tendon.

8. The device of claim 6, wherein the connective tissue is a ligament.

9. The device of claim 1, wherein the at least one sheet comprises multiple superimposed sheets.

10. The device of claim 1, wherein the at least one sheet is divided into two halves when connected to the elongate element.

11. The device of claim 1, wherein the at least one sheet is connected to the elongate element using surgical sutures.

12. The device of claim 1, wherein the biomechanical strength of the at least one sheet is equal to that of the elongate element.

13. A method of closing a midline incision, comprising the steps of:
providing an implant comprising an elongate element having a first longitudinal axis and at least one sheet connected to the elongate element along the first longitudinal axis, wherein the at least one sheet comprises an acellular dermal tissue matrix derived from porcine dermis having a Young's modulus within a range of 49.5 MPa to 94.7 MPa;
positioning the elongate element along the midline incision; and
positioning the at least one sheet on at least one of an anterior side and a posterior side of a rectus abdominis muscle surrounding the midline incision.

14. The method of claim 13, further comprising the step of creating spaces on the anterior or posterior sides of the rectus abdominis muscle for placement of the at least one sheet.

15. The method of claim 13, further comprising the step of suturing the at least one sheet to the rectus abdominis muscle.

16. The method of claim 13, wherein the at least one sheet is inserted between an anterior layer of fascia and the rectus abdominis muscle.

17. The method of claim 13, wherein the at least one sheet is inserted between a posterior layer of fascia and the rectus abdominis muscle.

18. The method of claim 13, wherein the at least one sheet is inserted over an anterior layer of fascia.

19. The method of claim 13, wherein the at least one sheet is inserted below a posterior layer of fascia.

20. The method of claim 13, wherein the acellular dermal tissue matrix is treated to remove antigens that are immunogenic to a human recipient.

21. The method of claim 13, wherein the elongate element comprises a piece of acellular connective tissue.

22. The method of claim 21, wherein the connective tissue comprises a tendon.

23. The method of claim 21, wherein the connective tissue comprises a ligament.

24. The method of claim 13, wherein the at least one sheet has a biomechanical strength that is equal to that of the elongate element.

25. The method of claim 13, wherein the at least one sheet has a stretchability that is equal to that of the elongate element.

* * * * *